United States Patent
Pirani et al.

(10) Patent No.: US 6,912,048 B2
(45) Date of Patent: Jun. 28, 2005

(54) METHOD AND DEVICE FOR IDENTIFYING FOREIGN BODIES IN A TEXTILE MATERIAL

(75) Inventors: Peter Pirani, Grüt/Gossau (CH); Hans Wampfler, Zürich (CH)

(73) Assignee: Uster Technologies AG, Uster (CH)

( * ) Notice: Subject to any disclaimer, the term of this patent is extended or adjusted under 35 U.S.C. 154(b) by 0 days.

(21) Appl. No.: 10/483,295

(22) PCT Filed: Jul. 4, 2002

(86) PCT No.: PCT/CH02/00364

§ 371 (c)(1),
(2), (4) Date: Mar. 22, 2004

(87) PCT Pub. No.: WO03/008950

PCT Pub. Date: Jan. 30, 2003

(65) Prior Publication Data

US 2004/0156044 A1 Aug. 12, 2004

(30) Foreign Application Priority Data

Jul. 12, 2001 (CH) ............................. 1281/01

(51) Int. Cl.⁷ ............................................. G01N 21/88
(52) U.S. Cl. .............................. 356/238.3; 356/238.2; 250/559.41; 250/559.45
(58) Field of Search ......................... 356/238.1–238.3, 356/237.1, 430; 250/559.41, 559.45, 221, 223 R, 559.42, 559.27; 209/576

(56) References Cited

U.S. PATENT DOCUMENTS

| | | | | |
|---|---|---|---|---|
| 5,383,017 A | * | 1/1995 | Schurch ................... | 356/238.3 |
| 5,414,520 A | * | 5/1995 | Joss et al. .................... | 356/430 |
| 5,499,794 A | * | 3/1996 | Aeppli .................. | 250/559.45 |
| 5,533,145 A | * | 7/1996 | Shofner et al. ............. | 382/141 |
| 5,636,803 A | * | 6/1997 | Aschmann et al. ...... | 242/473.5 |
| 6,064,478 A | * | 5/2000 | Paul et al. ................ | 356/237.1 |
| 6,175,408 B1 | * | 1/2001 | Henze et al. ............. | 356/238.3 |
| 6,201,602 B1 | | 3/2001 | Bouvyn | |
| 6,346,819 B1 | | 2/2002 | Joss et al. | |
| 6,380,548 B1 | * | 4/2002 | Henze et al. ............. | 250/559.4 |
| 6,552,290 B1 | * | 4/2003 | Lawandy .................... | 209/576 |
| 6,771,365 B1 | * | 8/2004 | Pirani et al. ............. | 356/238.2 |
| 2003/0107729 A1 | | 6/2003 | Furter | |

FOREIGN PATENT DOCUMENTS

| | | | |
|---|---|---|---|
| CH | 674379 | * | 5/1989 |
| DE | 297 19 245 | | 3/1998 |
| EP | 0 652 432 | | 5/1995 |
| EP | 1 058 112 | | 12/2000 |
| WO | 95 29396 | | 11/1995 |
| WO | 00 73771 | | 12/2000 |

* cited by examiner

Primary Examiner—Gregory J. Toatley, Jr.
Assistant Examiner—Sang H. Nguyen
(74) Attorney, Agent, or Firm—Burns, Doane, Swecker & Mathis, L.L.P.

(57) ABSTRACT

In a method and a device for identifying foreign bodies in a base textile material, the base textile material is subjected to beams and the beams reflected on the base material are detected and converted into an electrical signal. In order to detect foreign bodies in the material in a targeted manner and to differentiate them from each other, so all or only the unwanted foreign bodies can be, for example, eliminated, the beams have two defined and different wavelength ranges and the reflected beams are simultaneously and jointly detected from the two wavelength ranges. Preferably, a first defined wavelength range can be selected in such a way that the beams reflected on the base material provide random values in the electrical signal, for at least two different foreign bodies, and another defined wavelength range for the beams is selected in such a way that the reflected beams provide an electrical signal for the two foreign bodies, in a different ratio from the first wavelength range. The device contains a radiation source for radiation in at least two wavelength ranges, and a receiver for measuring the beams which are fully reflected by the material.

9 Claims, 3 Drawing Sheets

METHOD AND DEVICE FOR IDENTIFYING FOREIGN BODIES IN A TEXTILE MATERIAL

This disclosure is based upon Swiss Application No. 1281/01, filed on Jul. 12, 2001, and International Application No. PCT/CH02/00364, filed on Jul. 4, 2002, the contents of which are incorporated herein by reference.

BACKGROUND OF THE INVENTION

The invention relates to a method and to a device for identifying foreign bodies in a base textile material, wherein the base textile material is subjected to radiation, and the radiation reflected on the base material is detected and converted into an electrical signal.

Base textile material is here taken to mean, for example, a fibre composite made of textile fibres such as a strip, a roving yarn, a yarn made, for example, of cotton or polyester fibres or mixtures thereof, etc. or a composite made of a fibre composite of this type such as a nonwoven, a woven, a knitted fabric, etc. A base textile material is taken to mean a base material which can contain foreign bodies but is predominant in terms of quantity. Such foreign bodies are, for example, foreign fibres in the fibre composite, portions of plastic films which, for example, are reduced in size to form narrow strips or fibres, vegetable matter (such as husk contents) of the cotton and other unwanted substances, such as hairs, feathers, etc. which can occur as plant components.

A method of this type and a device are known from WO 95/29396. Here, the base material, for example a yarn, is irradiated, with white light from one light source or alternately with light of various wavelengths i.e. for example yellow, green or red light from various light sources, against an absorbent background. The light reflected by the base material is detected by at least one receiver which detects the spectrally different portions of the radiation at different times. Therefore, a single receiver can alternately receive the various colours or an individual receiver can be provided for each colour, so all colours are simultaneously detected by different receivers. The receiver or receivers generate(s) a respective electrical signal corresponding to the preferably received wavelength of the radiation. These signals are then brought into a relation with one another, for example balanced with one another, in order to compensate for unwanted effects. Such an unwanted effect may, for example, be that the reflected light depends not only on the colour of the yarn and of the foreign body but also on the mass, volume or diameter of the yarn. The effect of the mass or the volume, for example, can be eliminated by said balancing, so, for example, only the effect of the colour of the yarn can be identified. A foreign body in the material can thus be reliably identified.

SUMMARY OF THE INVENTION

One drawback of this method or device is to be seen in that processing of the signals is complex as the signals of the individual colour or wavelength fractions have to be separated either in terms of time by a plurality of clocked light sources or in terms of location by filters. The individual signals are then also separately processed and subsequently balanced together or jointly further processed. However with a plurality of different foreign bodies which are spatially distributed in the base material, the known method does not allow the individual foreign bodies to be separately detected, so a distinction can be made between the different foreign bodies in order, for example, to eliminate individual foreign bodies from the base material and to consciously leave others in the base material.

It is therefore the object of the invention to avoid said drawbacks and to propose a method and a device allowing different foreign bodies in the base material to be detected in a targeted manner such that they can also be distinguished from one another, so all or only the unwanted foreign bodies can be identified and, for example, eliminated. This opportunity should therefore be provided, in particular, when there is an initial suspicion that two or more different types of foreign body could be present.

To achieve this object the starting point is that the extent of the reflection of beams on the base textile material and on possible foreign bodies is at least partially known and that there are differences in the extent of the reflection which result as a function of the wavelength of the beams used. While, for example, the base material cotton has a constant course of reflection as a function of changes in the wavelength of the beams, this does not apply to all possible foreign bodies. It can be that certain foreign bodies have a virtually arbitrary seeming course and at certain wavelengths the beams reflect as strongly as the base material but at other wavelengths much less so or much more so. Therefore, depending on the wavelength of the beams, the foreign bodies can also reflect the beams equally strongly or at different strengths.

It is advantageous to first of all gain knowledge of how the base material and how the foreign bodies being sought reflect beams in the selected wavelength ranges.

It is crucial that the emitted beams have substantially two defined and different wavelength ranges and that the reflected beams are detected simultaneously and jointly for both wavelength ranges. Defined wavelength range is taken to mean a wavelength range with a certain spectral distribution about a central wavelength. The defined wavelength range is narrow-band.

A first defined wavelength range of the beams should be selected in a targeted manner such that the beams reflected by the base material provide first values in the electrical signal for at least two different foreign bodies. The values can be any values. A second defined wavelength range should then be selected for the beams such that the reflected beams produce second values in the electrical signal for the foreign bodies. These values are not in the same ratio for the two foreign bodies as in the corresponding electrical signals in the first wavelength range. The power of the beams in the two wavelength ranges should be selected such that the reflected radiation produces different values for the two foreign bodies.

This can be achieved with one or more radiation sources which direct beams in these two wavelength ranges onto the base material, in which sufficient distinctions can be expected for the two foreign bodies with respect to the intensity of the reflection. A single receiver is used to measure the beams fully reflected by the base material.

The beams should preferably be mixed, provided they originate from different radiation sources, so a homogenised beam mixture strikes the base material. The overall radiation irradiated therefrom is then proportional to the total contributions of the reflections in the individual wavelength ranges. This total radiation can therefore be simultaneously detected in a single sensor. This also emits a signal which can be used directly, for example to actuate a separating device, with which any portion of the base material which contains unwanted foreign bodies can be removed.

BREIF DESCRIPTION OF THE DRAWING

The advantages achieved by the invention are to be seen, in particular, in that certain foreign bodies can thus be searched for in a targeted manner in a base textile material. It is therefore possible to select which foreign bodies can be purposefully removed and which, if need be, can be left in the base material. If separate and controllable radiation sources are provided, the device can adapt the mode of operation, for example to other foreign bodies which suddenly or gradually remove or supplement the originally present foreign bodies in the same base material, in that the intensity of the beams with the two wavelength ranges is adapted to the changing conditions. The device may thus also be continuously adapted to the needs of the operator or customer. For example, it can thus be determined whether vegetable foreign bodies are to be eliminated or left in the base material. When, owing to the selected design of the device, it is possible to adapt the; relative intensity of the beams in the two wavelength ranges, the degree of elimination of the vegetable foreign bodies can also be controlled by adapting the sensitivity of the connected clearer.

The invention will be described in more detail hereinafter with the aid of an example and with reference to the accompanying drawings, in which:

FIGS. 1, 2 and 3 each show a view of a foreign body in a base material,

FIG. 4 shows a simplified view of reflections from the base material and from the foreign bodies by beams in different wavelength ranges, FIG. 5 shows a schematic and combined view of the signals generated according to the invention for the base material and for different foreign bodies, FIG. 6 is a schematic view of a device according to the invention and FIGS. 7, 8, 9 and 10 each show a schematic view of a portion of the device.

DETAILED DESCRIPTION OF THE INVENTION

The method according to the invention and the device are to be described hereinafter with reference to an example in which the base material is formed by a yarn.

Figure 4:
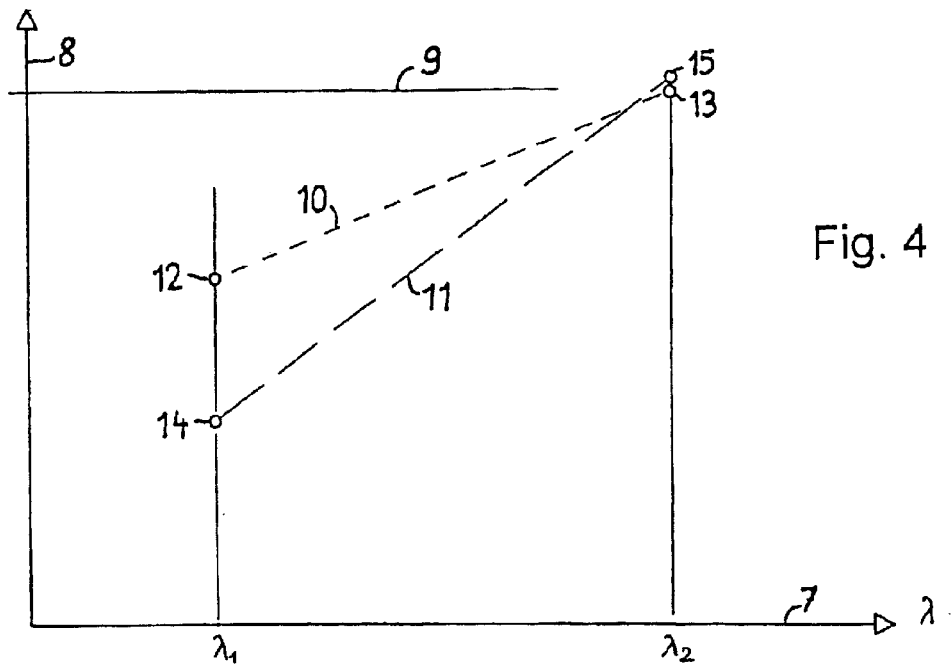

FIG. 4 shows a graph with an axis 7 along which values for the wavelength are plotted and an axis 8 along which values for the extent of the reflection of beams are plotted. In this graph various lines are drawn in, namely a line 9 for the base material, for example cotton, a short interrupted line 10 for a first foreign body F1 and an interrupted line 11 for a second foreign body F2. In order to make the example approximate a potentially real task somewhat more concretely, it can, for example, be assumed that the first foreign body F1 could be taken to mean vegetable material and the second foreign body F2 to be taken to mean red fibres made of films. This is to be understood as merely a selection of possible examples of foreign bodies. Line 9 corresponds to a reference value for the reflection of the beams on the provided base material alone. Lines 10 and 11 connect selected points 12, 13, 14 and 15 which represent measured values of the reflection for a specific wavelength $\lambda_1$, $\lambda_2$. Lines 10 and 11 do not indicate a course of the reflection as a function of the wavelength between the points 12 and 15 but merely serve to make the points which correspond to the same foreign body easier to identify.

Figure 5:
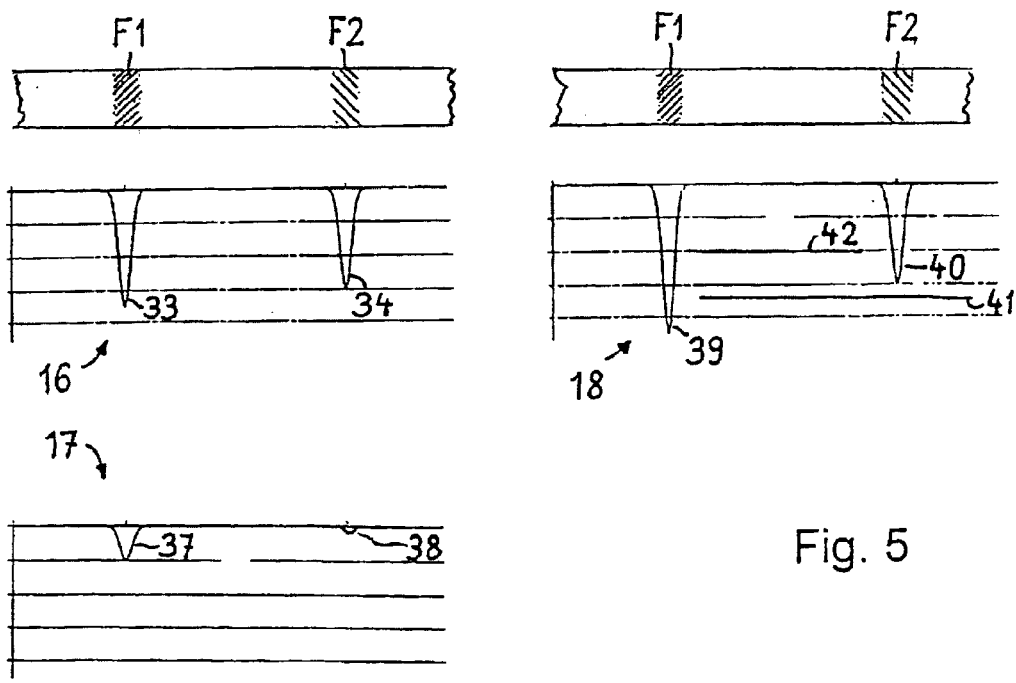

FIG. 5 shows schematically a respective portion of the base material or, in particular, of a yarn with a first foreign body F1 and a second foreign body F2. Electrical signals 16 and 17 generated by reflection are indicated for radiations $\lambda_1$, $\lambda_2$. A signal 18 results for mixed beams which consist of two wavelength ranges $\lambda_1$ and $\lambda_2$. The horizontal portions of these signals correspond to values for the reflection of the radiation on the pure base material or on the uncontaminated yarn, while downwardly pointing deflections correspond to values for the reflection as can be generated by foreign bodies. The causes and significance of the individual deflections are to be discussed in more detail in conjunction with the description of the mode of operation of the invention.

Figure 6:
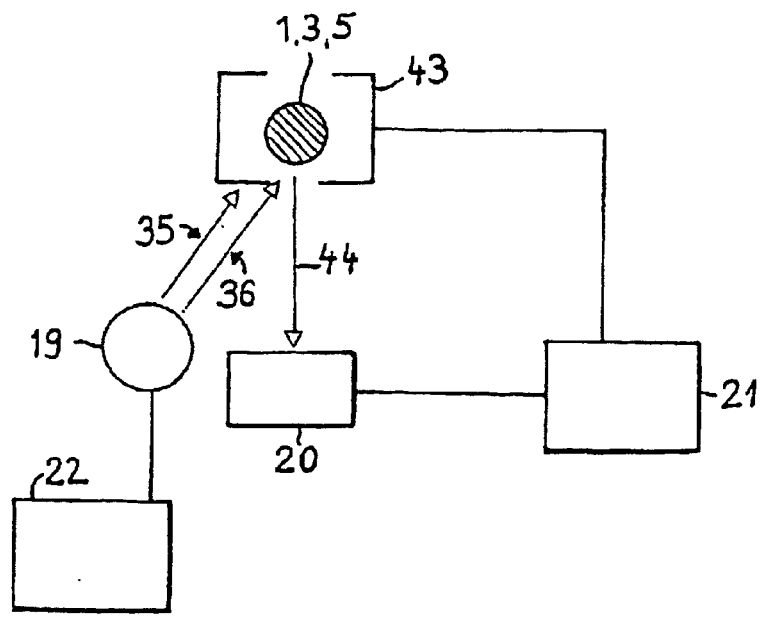
Figure 1:
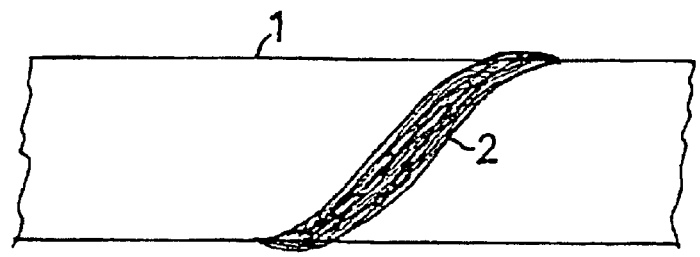
FIG. 1 shows a base material or yarn 1 which has a piece of film as the foreign body 2, the film being wound spirally around the yarn.
Figure 2:
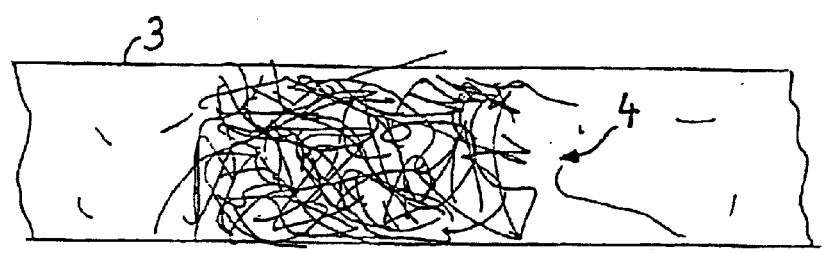
FIG. 2 shows a base material as a strip, nonwoven or yarn 3 which has an accumulation of individual fibres as the foreign body 4, the fibres having a different colour to the base material.
Figure 3:
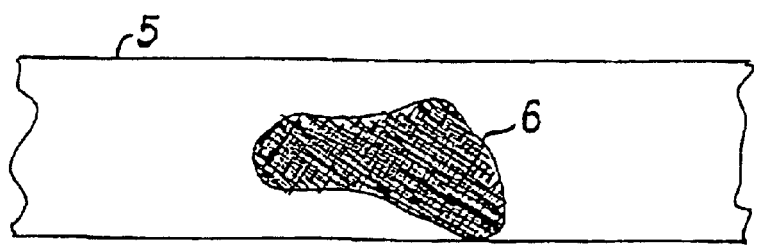
FIG. 3 shows a base material as a strip, nonwoven or yarn 5 which has an inclusion or a compact structure, such as any foreign body, a husk content of the cotton plant, a nep, etc. as the foreign body 6.

FIG. 6 shows a simplified view of a device for carrying out the method according to the invention. This consists of a radiation source 19, a receiver 20 for the radiation 44 reflected on the base material 1, 3, 5 and an evaluating unit 21 for the electrical signals emitted by the receiver 20. The radiation source 19 can also be connected to a controller 22. The radiation source 19 consists, for example, of an LED as a source for beams with a first wavelength and a further LED as a source for beams with a second wavelength. An, if need be, metered supply for the two sources or switching on or off of one source takes place via the controller 22.

Figure 7:
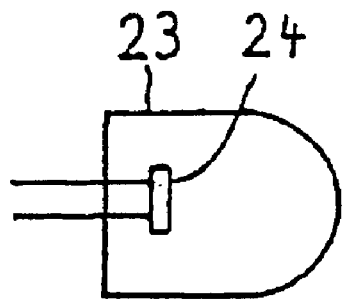

FIG. 7 shows as an embodiment for a radiation source 19 a light-emitting diode 23 known per se (called an LED, as is known) with a chip 24 which can irradiate beams in a preferably first defined wavelength range and, additionally, beams in a second defined wavelength range even if at different strength.

Figure 8:
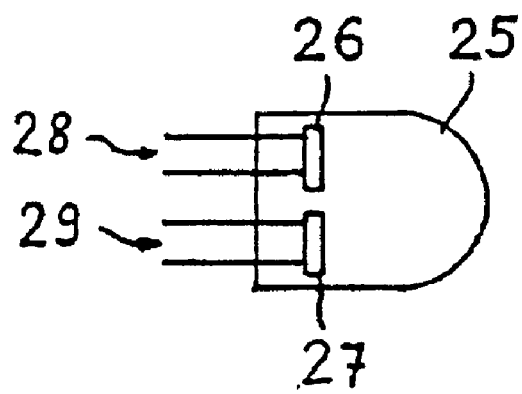

FIG. 8 shows a light-emitting diode 25 with two chips 26 and 27 mounted in the same housing, each chip 26, 27 radiating with its own wavelength and also having its own terminals 28, 29 for this purpose.

Figure 9:
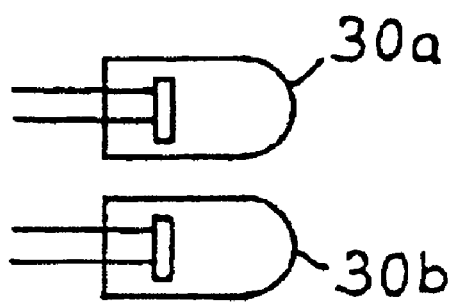

FIG. 9 shows as an embodiment for a radiation source 19 two light-emitting diodes 30a and 30b arranged side-by-side, each of which is suitable for beams in its own defined wavelength range.

Figure 10:
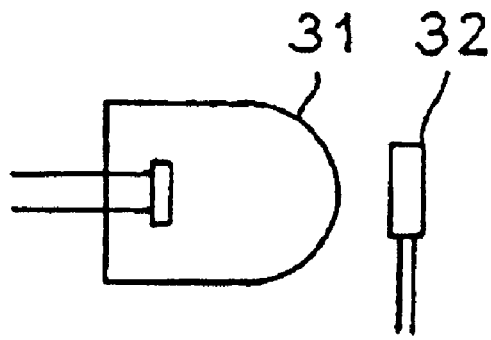

FIG. 10 shows as the radiation source 19 two light-emitting diodes 31 and 32 connected in series, the light-emitting diode 32 being designed as a "chip-LED".

The mode of operation of the invention is as follows:

If, for example, it is a matter of identifying a first foreign body F1 in a base material 1, 3, 5 a wavelength range $\lambda_1$ or $\lambda_2$ is selected according to FIG. 4, in which the foreign body reflects the emitted beams sufficiently strongly that an electrical signal is produced which differs sufficiently from that of the base material. This would certainly be the case for the foreign body is represented by lines 10 and 11 at $\lambda_1$. The electrical signal 16 which is produced in the process and which quantifies the reflection for beams with $\lambda_1$ results, according to FIG. 5, in a large deflection or value 33 for the foreign material F1 and a likewise very large deflection or value 34 for the foreign material F2. This means that in this case the foreign bodies F1 and F2 can be easily identified. However, in practice it is difficult to distinguish between F1 and F2 because of the small difference between the deflections or values 33 and 34.

By looking at FIG. 4, it can be seen that with a radiation source 19, which emits beams with a wavelength A2, it will be difficult to distinguish the foreign bodies F1 and F2 from each other and also from the base material, as line 9 characterises. A signal course 17 in FIG. 5, as is to be expected at the output of the receiver 20, with deflections or values 37 and 38, confirms this.

However, if a radiation source 19 according to the invention is used, which can emit beams 35, 36 at two different wavelength ranges, a signal course 18 may thereby be achieved at the output of the receiver 20. Beams with the two wavelength ranges $\lambda_1$ and $\lambda_2$ result in a deflection or value 39 for the foreign body F1 and in a deflection or value 40 for the foreign body F2. It can immediately be identified that, in comparison to the signal course 16, the deflections 39 and 44 for the foreign bodies F1 and F2 differ more from each other than the deflections 33 and 34 of the signal course 16. Therefore, it is possible here to set a limit 41 between the maximum values or deflections 39 and 40 to discriminate between the foreign bodies F1 and F2. If the limit 41 is exceeded by the signal course 18 foreign bodies F1 are identified. If, in addition, the limit 42 below the value or deflection 40 is stipulated, it can be established whether signal 18 is indicating foreign body F1 only, foreign body F2 only or both foreign bodies F1 and F2. In other words, the foreign bodies F1 and F2 are identified together when the signal 18 exceeds the limit 42. Foreign bodies F1 are identified when the signal 11 exceeds the limit 41.

It is thus possible to detect foreign bodies F1 and F2 separately. In this case, the signal course 18 is based on the assumption that, for example, 30% of the beams have the wavelength $\lambda_2$ and the remainder the wavelength $\lambda_1$.

With said method it is therefore possible, as shown, to either identify the foreign bodies F1 alone or else the foreign bodies F1 and F2 together. It is also possible to make the relative intensity of the two wavelength ranges selectable in order to thus eliminate, for example, vegetable matter to a variably selectable extent.

To carry out the method, the device should preferably be provided with a radiation source 19, wherein the power of the beams in one wavelength range can be controlled in comparison to the other wavelength range. This may be easily achieved with radiation sources, as shown by FIG. 8 to 10, and a controller 22 designed for this purpose.

By appropriately configuring the controller 22 it can also be ensured that the beams in at least one-wavelength range can be switched on and off. The operator can thus also easily adjust the unit to the base material or to other foreign bodies.

When processing cotton into yarn it can be important to restrict the number of interventions in a yarn clearer known per se. These interventions are made during the production of yarn using yarn clearers known per se, in particular with the cutting element thereof. However, it should be taken into account that the more foreign bodies that are identified and eliminated, the more frequently the production machine, i.e. the spinning frame or bobbin winding machine, is stopped. Therefore it is important to decide which foreign bodies are to be tolerated and which are to be cut out. This can be done, for example, in that a decision is made in advance on which foreign bodies in the end product are actually harmful and which are not. For example, vegetable matter is undesired as the foreign body but is also quite harmless as, for example, it does not impair the dyeability of the yarn and therefore cannot be easily identified in the woven. Beams in a wavelength range between 520 and 570 mm are suitable for identifying other foreign bodies, such as green, red or blue polypropylene film as the foreign body and for discriminating the vegetable matter. The polypropylene film would then substantially correspond to the foreign body F2, the vegetable matter, on the other hand, to the foreign body F1, with reference to the embodiments of FIGS. 4 and 5.

Beams, for example, with a wavelength in the infrared range are suitable for the second wavelength range $\lambda_2$.

If the device 43 for eliminating the foreign bodies from the base material, such as a yarn clearer known per se, is provided, this can be activated by the evaluating unit 21 as soon as the limit 41, 42 previously stored therein, for example in a processor, is reached or exceeded. The limits can be input into the evaluating 21 via an input device.

During the production of yarn, as can be assumed in this example, production can be optimised in this way such that a clear distinction can be made as to which foreign bodies are destructive, such that these are allowed to be removed, and this also always means that the production, i.e. the spinning head or the winding head, stands still for the time required for removal. If, therefore, it is clarified before production which foreign bodies are likely to the present in the base material and which foreign bodies are actually to be removed, the quality of the product can be increased thereby, on one hand, and, on the other hand, the production output is maintained in that, for example, the cutting rate of the yarn clearer is limited. If foreign bodies are to be identified in a roving yarn, strip or in a flat woven instead of in a yarn, as shown, then this merely has an effect on the dimensioning of the radiation sources and the receiver, but in particular on the device for cutting out the foreign bodies, if such a device is available.

We claim:

1. A method for identifying foreign bodies in a base textile material, comprising the steps of subjecting the textile material to beams of radiation that comprise two defined and different wavelength ranges, wherein the first defined wavelength range of the beams is selected such that the beams reflected by the base material with foreign bodies produce first values in an electrical signal for at least two different foreign bodies, and the second defined wavelength range is selected such that the reflected beams produce an electrical signal with two values for the same foreign bodies, which values are not in the same ratio for the two foreign bodies as in the corresponding electrical signals in the first wavelength range, and detecting the reflected beams simultaneously and jointly at the two wavelength ranges.

2. The method according to claim 1, further including the step of establishing a limit for the electrical signal which lies between values for the electrical signal of a first foreign body and of a second foreign body, to distinguish the foreign bodies from one another.

3. The method according to claim 1, further including the step of controlling the power of the beams in one wavelength range in comparison to the other wavelength range.

4. The method according to claim 1, further including the step of selectively switching the beams on and off in at least one wavelength range.

5. The method according to claim 1, wherein beams with a wavelength in the infrared range are selected for one wavelength range.

6. The method according to claim 1, wherein one wavelength range is capable of distinguishing disruptive foreign bodies in a base textile material comprising a yarn.

7. A device for identifying foreign bodies in a base textile material, comprising a radiation source for beams in at least two wavelength ranges, wherein the first defined wavelength range of the beams is selected such that the beams reflected by the base material with foreign bodies produce first values in an electrical signal for at least two different foreign bodies, and the second defined wavelength range is selected such that the reflected beams produce an electrical signal with two values for the same foreign bodies, which values are not in the same ratio for the two foreign bodies as in the corresponding electrical signals in the first wavelength range, and a receiver for simultaneously and jointly measuring the beams at said two wavelength ranges that are reflected by the base material.

8. The device according to claim 7, wherein said radiation source comprises a light-emitting diode, which radiates in two different wavelength ranges.

9. The device according to claim 7, wherein said radiation source comprises two light-emitting diodes, each of which radiates in a wavelength range which is different from that of the other light-emitting diode.

* * * * *